United States Patent [19]

Glover et al.

[11] 4,059,990

[45] Nov. 29, 1977

[54] MATERIALS HARDNESS TESTING DEVICE

[75] Inventors: Douglas Glover; Marvin J. Minter, both of Ann Arbor, Mich.

[73] Assignee: Federal-Mogul Corporation, Southfield, Mich.

[21] Appl. No.: 710,445

[22] Filed: Aug. 2, 1976

[51] Int. Cl.² .............................................. G01N 3/40
[52] U.S. Cl. ..................................................... 73/81
[58] Field of Search .................... 73/81, 85, 82, 83, 84

[56] References Cited

U.S. PATENT DOCUMENTS

| | | | |
|---|---|---|---|
| 2,685,197 | 8/1954 | Mennesson | 73/81 |
| 3,782,365 | 1/1974 | Pinna | 73/81 X |
| 3,934,463 | 1/1976 | Venderjagt | 73/81 |

Primary Examiner—Jerry W. Myracle
Attorney, Agent, or Firm—Harness, Dickey & Pierce

[57] ABSTRACT

A hardness testing device of the type adapted to measure the hardness of workpieces by indentation of the surface stratum thereof by an indenter or penetrating device. The depth of penetration of the workpiece under a prescribed load applied to the penetrating device is proportional to the hardness of the workpiece, which in turn is visually and/or audibly communicated by a variable fluid flow sensing system associated with the penetrating means. The testing device is readily adapted for automatic operation to test individual workpieces at commercial production rates to assure they are within prescribed quality and/or hardness limits.

17 Claims, 8 Drawing Figures

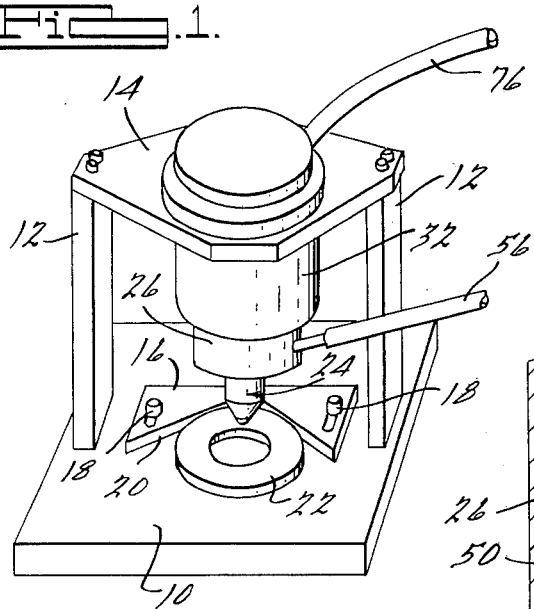
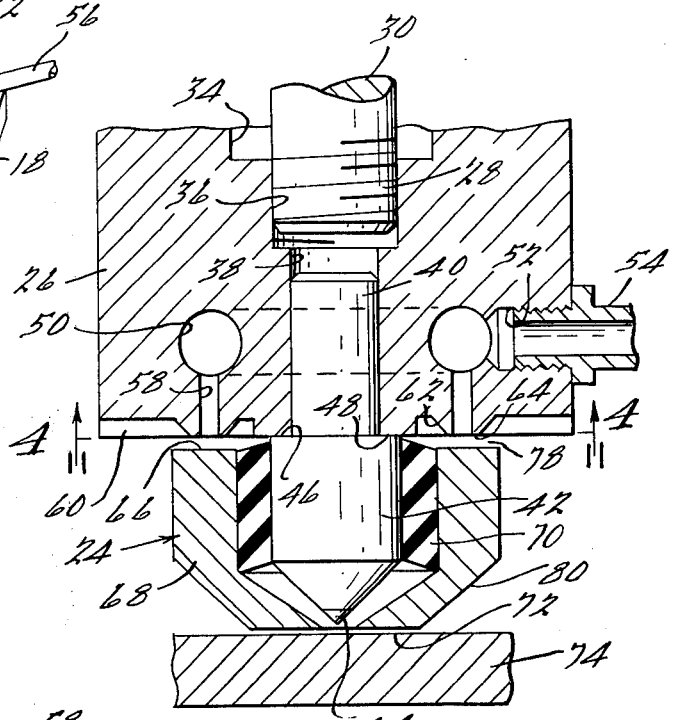
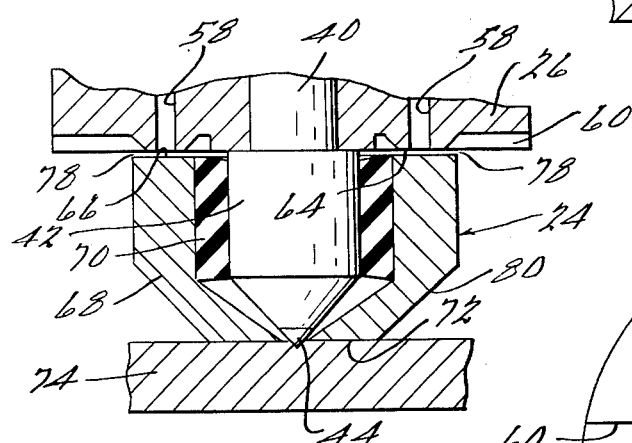
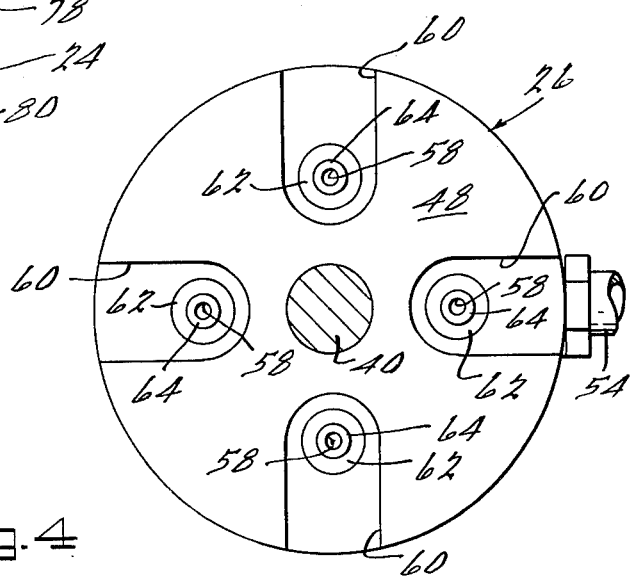

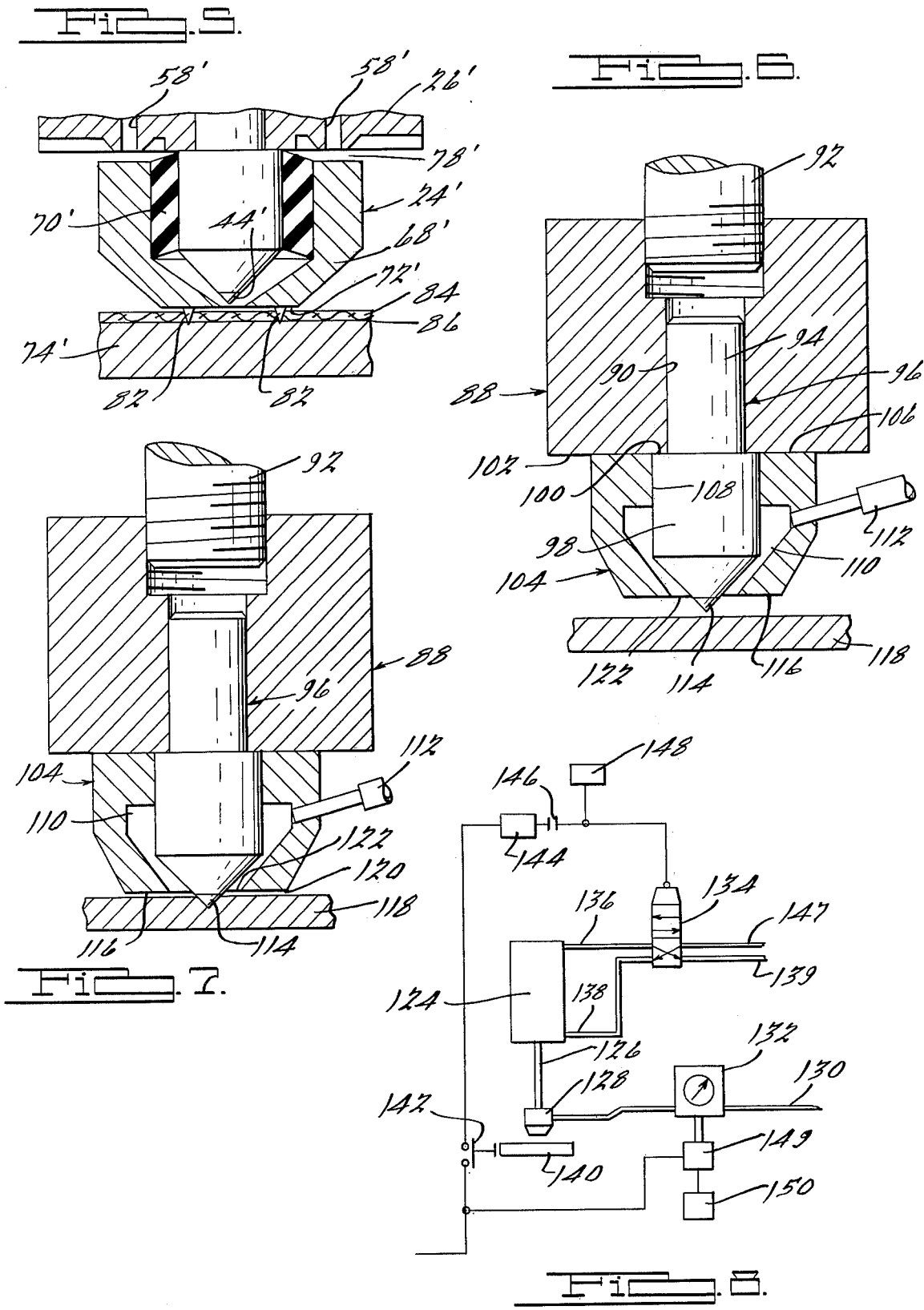

MATERIALS HARDNESS TESTING DEVICE

BACKGROUND OF THE INVENTION

Hardness testing devices of the various types heretofore known have primarily been based on the use of a hardened probe or indenter for penetrating the surface of a test piece under a prescribed load and measuring the depth of penetration as a function of the hardness of the surface stratum of such test piece. A variety of designs of probes or indenters have heretofore been used including ball-shaped indenters composed of hard material, such as metal carbide materials, as well as pyramidal-shaped indenters composed of industrial diamonds. Material hardness testers of the foregoing type employ a constant pressure and measure the depth of penetration, while others measure the pressure required to effect a penetration of the indenter into the surface stratum of a workpiece to a pre-established depth. In either case, the penetrating force required and the depth of penetration of the indentor are directed proportional to the hardness of the test piece.

While hardness testers of the types heretofore known have been satisfactory to provide accurate measurements of the hardness of workpieces and test pieces as a laboratory test device, their adaptation as a high-speed, automatic quality control device on a commercial production scale has not been effective due to the general tedious and time-consuming steps required in effecting a measurement of the hardness of the workpiece, as well as the sophistication of controls required and the costs associated in achieving fast and accurate readings. Problems have also been encountered with prior art testing devices in that the hardness masurement is taken between the indenter or penetrating probe and a supporting anvil on which the test piece is positioned such that any foreign matter between the anvil and the workpiece results in inaccuracies in the hardness reading of such devices.

The present invention overcomes many of the problems and disadvantages associated with prior art type materials hardness testers, which is of durable construction, rapid and substantially maintenance-free operation, which is of versatile use and can readily be adapted to different test conditions and workpieces, which can readily be adapted for automatic operation for measuring successive workpieces produced at commercial production rates, which can readily be adapted to produce an audible and/or visual signal identifying and/or rejecting test pieces which do not fall within a prescribed range of acceptable hardnesses and which is of economical cost and operation.

SUMMARY OF THE INVENTION

The benefits and advantages of the present invention are achieved by a materials hardness testing device including penetrating means supported on a framework for movement to and from a standby position spaced from the surface of a workpiece to be tested, and an indented test position in which the penetrater is disposed in embedded relationship in the surface stratum of the workpiece to a depth proportional to the hardness of the workpiece. The device includes means for applying a predetermined opposed force to the penetrating means and workpiece on movement to the test position, and further includes a fluid supply at a preselected pressure incorporating variable flow control means which are positionable in response to and in proportion to the depth of penetration of the penetrating means when in said test position. Sensing means are incorporated for sensing the condition of the fluid in the fluid supply as a function of the condition of the variable flow control means, which in turn is indicative of and can be directly translated into the degree of hardness of the test workpiece.

In accordance with one embodiment of the present invention, a collar encircling the penetrater is resiliently mounted for axial displacement in response to penetration of the penetrater into a workpiece and the axial displacement of the collar results in a proportional reduction in an air-flow gap incorporated in the fluid supply system, resulting in a variation in flow rate and/or pressure, which is sensed by a flow control meter and/or pressure gage. In accordance with an alternative embodiment, the collar encircles the penetrater and has a surface axially offset a preselected distance from the projecting end of the penetrater such that a supply of fluid discharged from an annular port provided in the face of the collar surface is subjected to a progressive reduction in flow rate and/or increase in pressure in proportion to the depth of penetration of the penetrater into the surface stratum of the workpiece. In accordance with still another embodiment of the present invention, the entire materials hardness testing device is formed with control means for effecting automatic sequential operation of individual workpieces and for signaling and/or mechanically rejecting workpieces which are of hardnesses falling outside of a predetermined permissible range.

Additional benefits and advantages of the present invention will become apparent upon a reading of the description of the preferred embodiments taken in conjunction with the accompanying drawings.

BRIEF DESCRIPTION OF THE DRAWINGS

FIG. 1 is a perspective view of a materials hardness testing device constructed in accordance with the preferred embodiments of the present invention;

FIG. 2 is a magnified fragmentary transverse vertical sectional view of the lower adapter and indenter assembly of the device shown in FIG. 1;

FIG. 3 is a fragmentary vertical sectional view of the adapter and indenter assembly shown in FIG. 2 after movement from a stand-by position into an indented test position;

FIG. 4 is a horizontal plan view, partly in section, of the lower face of the adapter shown in FIG. 2 as viewed along the line 4—4 thereof;

FIG. 5 is a fragmentary vertical transverse sectional view of an adapter and indenter assembly constructed in accordance with an alternative embodiment of the present invention;

FIG. 6 is a fragmentary vertical transverse sectional view of an adapter and indenter assembly constructed in accordance with still another alternative embodiment of the present invention, and illustrating the indenter assembly in the retracted stand-by position;

FIG. 7 is a fragmentary transverse sectional view of the adapter and indenter assembly shown in FIG. 6, but with the indenter assembly disposed in the indented test position; and FIG. 8 is a diagrammatic view of a control system for effecting automatic operation of the hardness testing device.

DESCRIPTION OF THE PREFERRED EMBODIMENTS

Referring now in detail to the drawings, and as may be best seen in FIG. 1, a materials hardness testing device of the present invention includes a framework comprising a base 10, a pair of spaced apart upright columns 12 supported on the base, to the upper ends of which a platform 14 is secured and extends therebetween. In the exemplary embodiment shown, a workpiece or test peice holder 16 is adjustably secured by means of screws 18 to the upper surface of the base 10 and is formed with a V-shaped edge 20 for appropriately positioning a workpiece, such as the annular ring 22, beneath an indenter assembly 24 of the testing device.

The indenter assembly 24, as best seen in FIGS. 1 and 2, is supported by an adapter 26, which in turn is removably secured to the threaded end portion 28 of a piston rod 30 of a double-acting fluid-actuated cylinder 32 having its upper portion secured to the platform 14 of the framework. The adapter 26 is formed with a centrally extending stepped bore 34, including a threaded section 36, which is threadably secured to the end portion 28 of the piston rod. A second axially aligned section 38 of the stepped bore is adapted to slidably receive a cylindrical shank 40 of a penetrater including an enlarged portion 42, the lower end of which is formed or provided with a conical configuration terminating in a hard wear-resistant point, such as a conical diamond point 44.

The specific configuration of the pointed end portion of the penetrater and the angularity of the cone or conical point can be varied as desired depending upon the hardness of the workpieces to be tested and the depth of penetration desired over the range of acceptable hardnesses to provide accuracy and reproducibility of the hardness readings. The conical or pyramidal configuration of the penetrating end of the penetrater portion 42 may conform to those utilized in other conventional hardness testing devices, such as Brinell, Rockwell and Vickers. In the Brinell hardness test, for example, the resistance of a material such as metal to plastic deformation by indentation of a hardened steel or carbide ball of a specified diameter under a specified load. The resultant hardness is expressed as Brinell hardness numbers, which is the result obtained by dividing the applied load in kilograms by the surface area of the impression in square millimeters. The Rockwell hardness test, on the other hand, determines hardness based on the depth of penetration of a specified penetrater into the specimen under certain arbitrarily fixed conditions of test. The Vickers hardness test is similar to the diamond pyramid hardness test in which a diamond pyramid indenter employing a 136° point is employed under variable loads to determine the hardness of various materials. By adopting indenters of the types employed in the various well known standardized hardness testing devices, a direct correlation can be made of the results obtained by the testing device of the present invention in terms of such standard numerical values.

The shank 40 of the indenter is removably retained in the bore section 34 of the adapter by a friction fit enabling quick replacement of the indenter in the event of wear or breakage, or replacement with an alternative type indenter in response to the measurement of different workpieces. This substantially increases the versatility of the test device. It will be understood that the indenter can also be threadably secured to the adapter or otherwise clamped or secured such as by a setscrew to removably retain the indenter with its annular radially extending shoulder 46 in firm seated engagement against the lower face 49 of the adapter.

As shown in FIGS. 1 and 2, the adapter 26 is provided with an internal annular plenum or chamber 50 which is disposed in communication with a radial port 52 in which a fitting 54 is threadably engaged having its outer end connected to a conduit 56 for supplying pressurized air under controlled conditions. A plurality of circumferentially spaced vertical ports 58 are formed in the face 48 of the adapter and extend upwardly therefrom into communication with the annular plenum 50. The face 48 of the adapter is formed with radially extending recesses 60, as best seen in FIGS. 2 and 4, adjacent to the outlet ends of the ports 58. The face of the adapter surrounding the discharge end of each of the ports 58 is formed with a tapered raised shoulder or raised boss 62 formed with an annular end face 64 disposed in the plane of the face 48 of the adapter.

The discharge ends of the ports 58 are positioned on a circle disposed concentric with the axis of the indenter assembly 24. In the specific embodiment shown, four ports are provided disposed at 90° arcuate intervals. The ports 58 and the encompassing annular shoulders 62 are disposed in vertical alignment with an annular face 66 of a collar 68 mounted by means of a resilient bushing 70 to the periphery of the enlarged portion 42 of the indenter. The resilient bushing 70 is suitably secured such as by an adhesive to the collar 68 and indenter portion 42 to prevent inadvertent axial movement therebetween. The lower portion of the collar 68 is formed with an annular contact face 72 which concentrically encircles the conical diamond point 44. The contact face 72 in a normal unstressed or stand-by position, as shown in FIG. 2, projects downwardly to a position slightly beyond the projecting end of the point 44.

Upon movement of the indenter assembly 24 and the adapter from the stand-by position as shown in FIG. 2 to a test position as shown in FIG. 3, the diamond point 44 penetrates and becomes indented into the surface of a test piece or workpiece 74 in response to an axial force applied thereto of a predetermined magnitude as controlled by the pressure of fluid supplied to the double-acting fluid-actuated cylinder through a supply tube 76 as shown in FIG. 1. As the indenter assembly moves from the stand-by position to the test position, the contact face 72 makes first contact with the upper surface of the test piece 74, whereafter further downward movement of the indenter assembly causes the resilient bushing 70 to deflect, whereby the collar 68 remains stationary during the course of further downward movement of the indenter and the adapter. Upon attaining the fully indented position, which is proportional to the hardness of the workpiece being tested, the annular face 66 of the collar is disposed a preselected distance from the annular end faces 64, defining therebetween a plurality of air escape gaps 78. The relative disposition of the annular face 66 and the end faces 64 define in combination a plurality of flow control devices regulating the escape of air through the ports 58 from the annular plenum 50. In accordance with the specific arrangement shown, the softer the workpiece, the greater the depth of penetration of the indenter, the greater the deflection of the resilient bushing, the greater the relative axial movement of the collar with respect to the indenter and the smaller the air escape gap 78, which causes a decreased flow of air and/or an increased pressure of the air in the annular plenum which can be sensed and is indicative of the relative hardness of the workpiece being tested. On the other hand, the greater the hardness of the workpiece, the less the depth of penetration of the indenter, the less the deflection of the resilient bushing, the less the magnitude of relative axial movement between the collar and the indenter, the greater the distance of the air escape gap and, accordingly, the greater the flow rate and/or the lower the pressure of the air in the annular plenum.

It will be appreciated from the foregoing that the provision of a plurality of discharge ports 58, such as the four ports shown in the embodiment illustrated in FIGS. 2-4, any sight misalignment between the axis of the indenter assembly and the surface of the test piece 74 will result in a slight skewing of the resiliently mounted collar 68, causing the air escape gaps 78 to vary from one side to the other. However, the provision of a plurality of such ports at substantially equal circumferentially spaced increments serves to average the deflection of the collar and the resultant flow rate and/or pressure increase in the annular plenum comprises an average reading compensating for any such misalignments.

The recesses or relieved areas 60 extending radially adjacent to the air escape gaps permits unrestricted passage of air without further disturbance to the atmosphere.

The lower portion of the collar 68 is preferably tapered such as indicated at 80 in FIGS. 2 and 3, whereby the total diameter and area of the contact surface 72 is proportionately reduced. The specific size of the contact face 72 can be varied consistent with the configuration and nature of the workpiece being tested, so as to provide proper contact with the upper surface thereof. Workpieces having irregularly-shaped surfaces require contact faces of relatively small diameter to assure surface contact only in the area immediately surrounding the point of indentation of the indenter. It is also contemplated that the end face 64 of the collar can be appropriately curved or contoured as may be desired so as to conform with the surface contour of the workpiece being tested.

A modified version of the materials hardness testing device is illustrated in FIG. 5 in which the same components have been designated by the same numerals with a prime affixed thereto. As shown in FIG. 5, the indenter assembly 24' and adapter 26' are identical to that previously shown and described in connections with FIGS. 2-4, with the exception that the contact face 72' of the collar 68' is provided with a plurality of needle-like or pointed projections which are adapted to penetrate a soft uneven surface layer 84 on the surface of the test piece 74' being tested. The presence of such an irregular compressible soft surface layer 84 would normally cause inaccuracies in the reading of the hardness due to variations in the thickness and compressibility thereof such that the variations in flow rate and/or pressure of the air discharged through the ports 58' would not necessarily be indicative of the true hardness reading as a function of depth of penetration of the test piece. By virtue of incorporating the needlelike projections 82, a penetration of the soft variable surface layer 84 is effected such that the contact face 72' is disposed in spaced parallel relationship with respect to the underlying surface interface 86. A penetration by the sharp projections 82 through the soft overlying layer 84 is readily accomplished by the light pressure supplied by a resilient deflection of the resilient bushing 70' during the downward movement of the indenter assembly and the indentation of the point 44' thereof into the underlying substrate. In accordance with the foregoing arrangement, more accurate measurements of hardness are achieved in spite of the presence of variable and irregular soft surface layers or liquid films on the workpieces being tested. The reduction in air flow as determined by the size of the air escape gaps 78' when the indenter assembly is in the test is proportional to the displacement of the point 44' of the indenter assembly relative to the position of the projecting ends of the projections 82 on the underlying interface 86. Such displacement remains essentially constant even though no intervening soft layer 84 is present on the workpiece being tested.

An alternative satisfactory embodiment of the materials hardness testing device previously described is shown in FIGS. 6 and 7. The testing device is similar to that illustrated in FIG. 1, but the adapter and indenter assemblies are modified insofar as the arrangement of plenums and passageways for effecting a restriction in their flow rate in proportion to the depth of penetration of the indenter assembly. As shown in FIG. 6, an adapter 88 is formed with a stepped throughbore 90 in the upper portion of which the threaded end of a piston rod 92 is disposed in threaded engagement. A shank 94 of an indenter 96 is frictionally engaged in the lower portion of the throughbore and an enlarged portion 98 of the indenter 96 is positioned with the face 100 of an annular shoulder in firm seating abutting relationship against the underface surface 102 of the adapter 88.

An annular collar 104 is rigidly mounted around the enlarged portion 98 of the indenter, with the upper annular shoulder 106 thereof disposed in firm seated engagement against the underface surface 102 of the adapter 88. The annular collar 104 is retained in fixed disposition with respect to the enlarged portion 98 of the indenter by means of a friction fit, an adhesive, set screws or the like. An axial bore 108 extending through the upper portion of the annular collar 104 is disposed in sealing relationship around the head portion of the indenter to prevent any escape of pressurized air admitted into an annular plenum 110 through a supply pipe 112 connected to a source of pressurized air at controlled conditions.

The lower portion of the enlarged portion 98 of the indenter is of a conical configuration terminating in a diamond or pyramid point 114 which projects beyond the end face 116 of the collar 104. The axial offset between the end of the point 114 and the end face 116 is conveniently established at a distance slightly greater than the maximum depth of penetration of the indenter into a test piece, such as the workpiece 118, such that the end face 116 will be disposed in spaced relationship from the upper surface of the workpiece when the indenter is in the test position as shown in FIG. 7, forming an annular air gap 120. The interior of the annular plenum 110 is of a circular converging configuration forming in combination with the indenter portion at a position adjacent to the end face 116, an annular air discharge port 122.

The principle of operation of the testing device shown in FIGS. 6 and 7 is similar to that previously described. Upon movement of the adapter and indenter from a stand-by position as shown in FIG. 6 to a test position as shown in FIG. 7, the collar and indenter move in unison such that the end face 116 of the collar is positioned in spaced relationship from the surface of the workpiece 118, a distance proportional to the depth of penetration of the point 114 into the workpiece, which in turn is a function of the hardness of the workpiece. The height of the annular air gap 120, as shown in FIG. 7, constitutes a variable flow control device and regulates the pressure and/or flow rate of the regulated air introduced into the annular plenum through the supply tube 112. A sensing of the condition of the pressure and/or flow rate of the air calibrated with respect to the depth of indentation of the indenter in the workpiece provides a direct indication of the hardness of the workpiece being tested. It will be further observed in the arrangement as illustrated in FIG. 7 that any slight misalignment between the axis of the indenter and the surface of the test piece will cause a skewing of the end face 116 and a corresponding variation in the restriction provided along the annular air gap 120. Since the end face 116 is concentric with the axis of the penetrater, any such misalignment and variation in air gap is averaged out around the periphery thereof, providing an average reading and automatically compensating for any such inadvertent misalignment problem.

The sequence of operation of the hardness testing device can be effected manually or can be automatically controlled in accordance with a timed sequence for testing consecutive workpieces produced in a manufacturing operation. A typical control system is schematically shown in FIG. 8, in which the materials testing device is shown as comprising a double-acting air-actuated cylinder 124 having its piston rod 126 connected to an indenter and adapter assembly or head 128 of any of the types shown in FIGS. 2–7 of the drawing. A supply of regulated control air is provided by a conduit 130 incorporating a sensing device, such as a pressure gauge 132, for sensing the difference in the condition of the control air between a stand-by position and a test position of the testing device.

Reciprocating movement of the actuating cylinder 124 between the stand-by and test position during which a preselected force is applied to the indenter assembly is achieved by a four-way solenoid-actuated valve 134 connected by conduits 136, 138 to the blank end and rod end, respectively, of the double-acting cylinder 124. The conduits 136, 138 alternatively are pressurized and vented during sequencing of the test device.

As shown in FIG. 8, a test piece 140 is manually or automatically placed in position in the testing device which effects actuation of electrical contact 142 which closes effecting the energization of a timing relay 144 which commences to time a preselected test time period. Upon energization, time relay 144 closes its normally open contact 146 causing an energization of the solenoid of the four-way solenoid valve 134 causing a regulated pressurized actuation air in supply line 147 to enter the conduit 136 and the blank end of the cylinder and to vent air from the rod end of the cylinder through conduit 138 and vent tube 139, whereby a controlled force is applied through the piston rod to the indenter assembly, effecting movement of the indenter assembly to the test position. Simultaneously, a counter 148 is energized.

As the indenter assembly 128 moves to the test position and becomes indented in the surface of the test piece 140, a restriction in the flow of control air is effected proportional to the hardness of the workpiece, which is sensed by and visually communicated by the gauge 132, which can be conveniently cablibrated in terms of pressure, deflection or suitable hardness unit. The gauge 132 is connected to a pressure switch 149 which is presettable so as to close its contacts when a certain pressure is exceeded, evidencing a test piece having insufficient hardness. An energization of the pressure switch 149 in turn causes a visual or audible alarm 150 to be energized, signaling the operator of the presence of a test piece not within the specified hardness limits. Alternatively, the alarm 150 can be in the form of an actuating gate or lever operative for mechanically transferring the test piece to a reject chute or bin for rework.

At the completion of the testing cycle as established by the timer, contacts 146 open causing the solenoid valve 134 to move to a position effecting retraction of the indenter head assembly and causing a resetting of the counter-coil. Upon retraction of the indenter head assembly to the stand-by position, a removal of the workpiece 140 can be effected manually or automatically, which causes switch 142 to open, deenergizing the timer relay coil 144 and causing this unit to reset preparatory to the next operating cycle.

While it will be apparent that the invention herein described is well calculated to achieve the benefits and advantages set forth, it will be appreciated that the invention is susceptible to modification, variation and change without departing from the spirit thereof.

What is claimed is:

1. A hardness testing device comprising a framework, a head including penetrating means supported by said framework for movement relative to a workpiece to and from a stand-by position spaced from the surface of the workpiece and an indented test position, means for applying a predetermined opposed force to said penetrating means and workpiece when in said test position to effect a penetration of the workpiece by said penetrating means to a depth proportional to the hardness of the workpiece surface stratum, fluid supply means for supplying fluid at a preselected pressure, variable flow control means associated with said fluid supply means movable to and from a first position when said penetrating means is in said stand-by position and a variable second position when said penetrating means is in said test position in proportion to the depth of penetration of said penetrating means, said variable flow control means comprising a member resiliently mounted on said head and including an engaging end positioned axially beyond the end of said penetrating means and adapted to contact the surface of a workpiece being tested in a region adjacent to the point of penetration of said penetrating means, said member movable through an axial displacement relative to said penetrating means in response to movement of said penetrating means to said test position, said axial displacement of said member being proportional to the depth of penetration of said penetrating means, said member including a portion defining an orifice of a size variable in proportion to said axial displacement of said member when in said second position, said orifice disposed in communication with said fluid supply means providing a variable restriction of flow of said fluid through said orifice and a corrresponding change in the condition of said fluid indicative of the hardness of the workpiece, and sensing means associated with said fluid supply means for sensing the condition of the fluid therein when said penetrating means is in said test position as indicative of the hardness of the workpiece.

2. The testing device as defined in claim 1, in which said variable flow control means includes a member defining an orifice disposed in communication with said fluid supply means, said orifice defining a passageway of variable size when in said second position in proportion to the depth of penetration of said penetrating means.

3. The testing device as defined in claim 1, wherein said sensing means comprises a pressure gauge.

4. The testing device as defined in claim 1, wherein said sensing means comprises a flow meter.

5. The testing device as defined in claim 1, wherein said sensing means includes presettable means for signaling a condition of hardness beyond a preselected limit.

6. The testing device as defined in claim 1, in which said member is in the form of a collar encircling said penetrating means and resiliently supported thereon.

7. The testing device as defined in claim 1, in which said member includes a first surface disposed in spaced relationship from a second surface of said head defining therebetween said orifice of variable size.

8. The testing device as defined in claim 7, wherein said head further includes a plenum chamber disposed in communication with said fluid supply means and a plurality of ports formed in said head extending between said plenum and said second surface and in communication with said orifice.

9. The testing device as defined in claim 1, in which said first and said second surface are of an annular configuration and are arranged concentrically around the axis of said penetrating means, and wherein said plurality of ports are arranged in a circular pattern at substantially equal circumferentially spaced increments in relationship to said first surface.

10. The testing device as defined in claim 1, in which said engaging end of said member is provided with at least one needlelike projection for contacting the surface of a workpiece being tested.

11. A hardness testing device comprising a framework, a head including penetrating means supported by said framework for movement relative to a workpiece to and from a stand-by position spaced from the surface of the workpiece and an indented test position, means comprising a double-acting fluid-actuated cylinder connected to a supply of fluid at a controlled pressure for applying a predetermined opposed force to said penetrating means and workpiece when in said test position to effect a penetration of the workpiece by said penetrating means to a depth proportional to the hardness of the workpiece surface stratum, fluid supply means for supplying fluid at a preselected pressure, variable flow control means associated with said fluid supply means movable to and from a first position when said penetrating means is in said stand-by position and a variable second position when said penetrating means is in said test position in proportion to the depth of penetration of said penetrating means, and sensing means associated with said fluid supply means for sensing the condition of the fluid therein when said penetrating means is in said test position as indicative of the hardness of the workpiece.

12. A hardness testing device comprising a framework, a head including penetrating means supported by said framework for movement relative to a workpiece to and from a stand-by position spaced from the surface of the workpiece and an indented test position, control means for effecting movement of said penetrating means to and from said stand-by and said test position in a preselected time sequence in response to the positioning of a workpiece to be tested in appropriate position on said testing device, means for applying a predetermined opposed force to said penetrating means and workpiece when in said test position to effect a penetration of the workpiece by said penetrating means to a depth proportional to the hardness of the workpiece surface stratum, fluid supply means for supplying fluid at a preselected pressure, variable flow control means associated with said fluid supply means movable to and from a first position when said penetrating means is in said stand-by position and a variable second position when said penetrating means is in said test position in proportion to the depth of penetration of said penetrating means, and sensing means associated with said fluid supply means for sensing the condition of the fluid therein when said penetrating means is in said test position as indicative of the hardness of the workpiece.

13. A hardness testing device comprising a framework, a head including penetrating means supported by said framework for movement relative to a workpiece to and from a stand-by position spaced from the surface of the workpiece and an indented test position, means for applying a predetermined opposed force to said penetrating means and workpice when in said test position to effect a penetration of the workpiece by said penetrating means to a depth proportional to the hardness of the workpiece surface stratum, fluid supply means for supplying fluid at a preselected pressure, variable flow control means associated with said fluid supply means movable to and from a first position when said penetrating means is in said stand-by position and a variable second position when said penetrating means is in said test position in proportion to the depth of penetration of said penetrating means, said variable flow control means comprising a collar encircling the penetrating end of said penetrating means and defining a plenum disposed in communication with said fluid supply means and including a port surrounding said penetrating end of said penetrating means, said collar terminating along a plane disposed perpendicular to the direction of travel of said penetrating means and located at a distance axially spaced rearwardly from the tip of said penetrating end defining an annular edge, said annular edge defining in combination with the surface of a workpiece being tested an annular orifice of a variable height when in said second position providing a variable restriction of flow of said fluid through said orifice and a corresponding change in the condition of said fluid indicative of the hardness of said workpiece, and sensing means associated with said fluid supply means for sensing the condition of the fluid therein when said penetrating means is in said test position as indicative of the hardness of the workpiece.

14. The testing device as defined in claim 13, in which said variable flow control means includes a member defining an orifice disposed in communication with said fluid supply means, said orifice defining a passageway of variable size when in said second position in proportion to the depth of penetration of said penetrating means.

15. The testing device as defined in claim 13, wherein said sensing means comprises a pressure gauge.

16. The testing device as defined in claim 13, wherein said sensing means comprises a flow meter.

17. The testing device as defined in claim 13, wherein said sensing means includes presettable means for signaling a condition of hardness beyond a preselected limit.

* * * * *